United States Patent [19]
Hossain et al.

[11] Patent Number: 5,778,039
[45] Date of Patent: Jul. 7, 1998

[54] METHOD AND APPARATUS FOR THE DETECTION OF LIGHT ELEMENTS ON THE SURFACE OF A SEMICONDUCTOR SUBSTRATE USING X-RAY FLUORESCENCE (XRF)

[75] Inventors: Tim Z. Hossain; John K. Lowell, both of Round Rock, Tex.

[73] Assignee: Advanced Micro Devices, Inc., Sunnyvale, Calif.

[21] Appl. No.: 604,257

[22] Filed: Feb. 21, 1996

[51] Int. Cl.$^6$ .................................................. G01N 23/223
[52] U.S. Cl. ............................. 378/45; 378/44; 378/49
[58] Field of Search ............................ 378/44, 45, 46, 378/49, 50, 84, 83

[56] References Cited

U.S. PATENT DOCUMENTS

| | | |
|---|---|---|
| 5,025,145 | 6/1991 | Lagowski . |
| 5,220,591 | 6/1993 | Ohsugi et al. ............................ 378/45 |
| 5,430,786 | 7/1995 | Komatsu et al. ......................... 378/45 |
| 5,471,293 | 11/1995 | Lowell et al. . |
| 5,537,451 | 7/1996 | Serebryakov et al. ................... 378/45 |

OTHER PUBLICATIONS

Lagowski et al., "Non–Contact Mapping of Heavy Metal Contamination for Silicon IC Fabrication," 1992, pp. A185–A192.

Moore, "Theory and Experiment on the Surface–Photovoltage Diffusion–Length Measurement as Applied to Amorphous Silicon," *American Institute of Physics*, 1983, pp. 222–228.

*Primary Examiner*—David P. Porta
*Attorney, Agent, or Firm*—Kevin L. Daffer; Conley, Rose & Tayon

[57] ABSTRACT

A method and apparatus are presented which provide non-intrusive detection of atoms of light elements (atomic numbers 3–13) on a surface of a semiconductor substrate using X-ray fluorescence (XRF). The present technique may be economically performed routinely on manufactured products. The method includes producing a monochromatic X-ray beam comprising X-ray photons with energy levels operably chosen to cause only atoms of light elements to emit secondary X-ray photons. The monochromatic X-ray beam is then focused onto a circular exposed region on the surface of the semiconductor substrate, the circular exposed region having a diameter ranging from about 0.5 mm to about 10.0 mm. Secondary X-ray photons emitted by atoms of light elements in the exposed region on the surface of the semiconductor substrate are directed to at least one X-ray detector. Each X-ray detector is aligned to receive secondary X-ray photons from a single light element, and is illuminated for a predetermined amount of time. The number of secondary X-ray photons detected by an X-ray detector in a predetermined amount of time is directly proportional to the number of atoms of a corresponding light element on the surface of the semiconductor substrate. The apparatus includes a high-power X-ray source, a first collimator, a first multilayer crystal, a focusing capillary, a second collimator, a second multilayer crystal, and at least one X-ray detector.

13 Claims, 5 Drawing Sheets

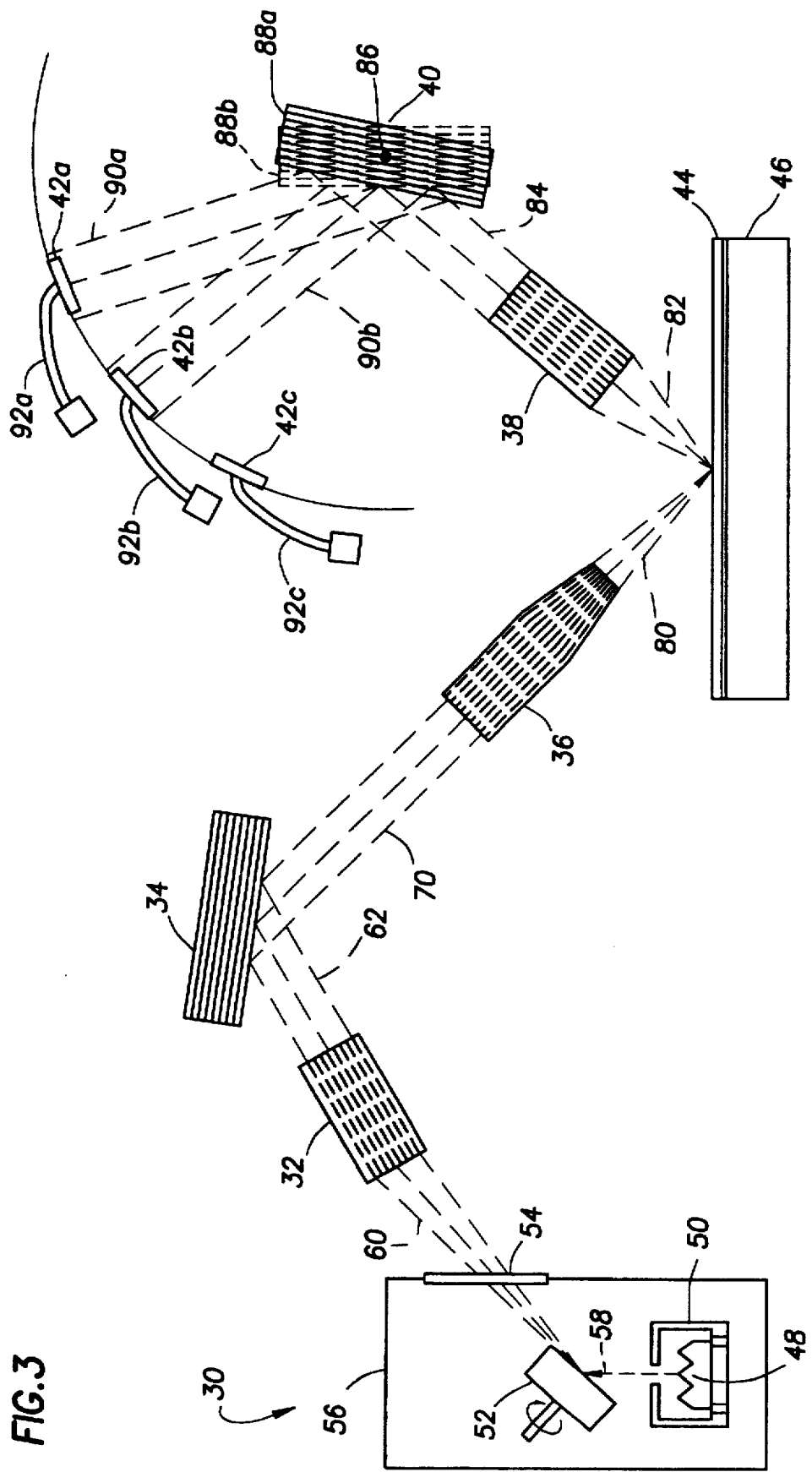

METHOD AND APPARATUS FOR THE DETECTION OF LIGHT ELEMENTS ON THE SURFACE OF A SEMICONDUCTOR SUBSTRATE USING X-RAY FLUORESCENCE (XRF)

BACKGROUND OF THE INVENTION

1. Field of the Invention

This invention relates to semiconductor wafer fabrication, more specifically to a non-intrusive apparatus and method for detecting the presence of light (low atomic mass) elements on the surface of a semiconductor substrate using X-ray fluorescence (XRF).

2. Description of the Relevant Art

In the manufacture of integrated circuits, many different kinds of contaminants may adversely affect processing yield, device performance, or device reliability. For example, the presence of mobile ionic contaminants (e.g., sodium and potassium ions) in dielectric layers of metal oxide semiconductor (MOS) devices are known to cause device reliability problems. Ionized sodium ($Na^+$) and potassium ($K^+$) atoms are very mobile in oxide layers, and tend to move through gate oxides of MOS devices under the influence of the electric fields generated between gate electrodes and substrates during device operation. Long term changes in MOS device threshold voltage levels may occur as the charged ions drift to the interface between the gate oxide and the underlying substrate. Changes in threshold voltage levels may become large enough to cause circuits which incorporate these MOS devices to fail to meet electrical or performance requirements.

The light (low mass) elements, with atomic numbers 3 through 13, include lithium, beryllium, boron, carbon, nitrogen, oxygen, fluorine, neon, sodium, magnesium, and aluminum. Of particular interest are carbon, magnesium, aluminum, and sodium. Common organic contaminants such as fingerprint oils contain the element carbon. Sodium is found in abundance in nature, and ionized sodium is the most prevalent mobile ionic contaminant in integrated circuits.

Current techniques for detecting the presence of atoms and ions on the surfaces of and within semiconductor substrates include secondary ion mass spectroscopy (SIMS), Auger emission spectroscopy (AES), and X-ray photoelectron spectroscopy (XPS). These quantitative analytical methods are surface analysis techniques. The depth profiling required for determining the concentrations of atoms in a sample requires repetition of the steps of surface analysis followed by removal of a thin layer of material at the upper surface of the sample. These techniques are very time consuming and are destructive in nature, requiring expendable samples. Such tests cannot be routinely performed economically, nor can they be performed directly on manufactured products.

It would thus be desirable to have a non-contact and non-destructive method and apparatus for the detection of light elements on a surface of a silicon substrate.

SUMMARY OF THE INVENTION

The problems outlined above are in large part solved by a method and apparatus providing non-intrusive detection of atoms of light elements (with atomic numbers between 3 and 13) on a surface of a semiconductor substrate using X-ray fluorescence (XRF). The present technique may be economically performed routinely on substrates upon which active semiconductor devices have been formed.

The present method includes producing a monochromatic X-ray beam comprising photons with energy levels capable of causing atoms of light elements to emit secondary X-ray photons. The monochromatic X-ray beam is then focused onto a circular area on the surface of the semiconductor substrate. The illuminated circular area has a diameter ranging from about 0.5 mm to about 10.0 mm. Secondary X-ray photons emitted by atoms of light elements on the surface of the semiconductor substrate are directed toward at least one X-ray detector. Each X-ray detector is aligned to receive secondary X-ray photons from a single light element, and is illuminated for a predetermined amount of time.

The present method allows examination of a target material from the surface of the target material down to a maximum escape depth of secondary X-ray photons emitted by atoms of light elements present within the target material. The maximum escape depth associated with a given element is determined chiefly by the energy levels of the secondary X-ray photons emitted by atoms of the element and the density of the target material. An exemplary escape depth associated with atoms of light elements present in silicon substrates used to fabricate integrated circuits is believed to be about 0.01 microns.

Absorption of a primary X-ray photon by an atom of a light element on the surface of the semiconductor substrate results in the emission of a single secondary X-ray photon. Thus for a given number of primary X-ray photons (with sufficient energy) incident upon the surface of the semiconductor substrate per unit time, the number of secondary X-ray photons detected by an X-ray detector in a predetermined amount of time is directly proportional to the number of atoms of a corresponding light element on the surface of the semiconductor substrate.

The present apparatus includes a high-power X-ray source, a first collimator, a first multilayer crystal, a focusing capillary, a second collimator, a second multilayer crystal, and at least one X-ray detector. The high-power X ray source produces divergent polychromatic X-ray radiation including photons with energy levels capable of causing atoms of light elements to emit secondary X-ray photons. The first collimator receives divergent polychromatic X-ray radiation from the high-power X-ray source and produces a quasi-parallel polychromatic X-ray beam. The first multilayer crystal receives the quasi-parallel polychromatic X-ray beam from the first collimator and produces a strongly-reflected monochromatic X-ray beam. X-ray photons of the monochromatic X-ray beam have energy levels capable of causing atoms of light elements to emit secondary X-ray photons. The focusing capillary receives the monochromatic X-ray beam from the first multilayer crystal and focuses the monochromatic X-ray beam onto a circular area on the surface of the semiconductor substrate. The illuminated circular area has a diameter ranging from about 0.5 mm to about 10.0 mm. The second collimator receives divergent polychromatic secondary X-ray photons emitted by atoms of light elements on the surface of the semiconductor substrate and produces a quasi-parallel polychromatic X-ray beam. The second multilayer crystal receives the quasi-parallel polychromatic X-ray beam from the second collimator and produces one or more strongly-reflected monochromatic X-ray beams. Photons of each monochromatic X-ray beam produced by the second multilayer crystal have an energy level corresponding to a characteristic secondary X-ray emission energy level of a light element. At least one X-ray detector is provided which is capable of detecting a photon of a monochromatic X-ray beam from the second multilayer crystal and producing an electrical output signal.

X-ray photons of the monochromatic X-ray beam produced by the first multilayer crystal have energy levels capable of causing atoms of light elements (with atomic numbers 3–13) to emit secondary X-ray photons, but do not have energy levels capable of causing atoms of heavier elements (with atomic numbers 14 and greater) to emit secondary X-ray photons. This is important in order to prevent the basic semiconductor material of the substrate (e.g., silicon, atomic number 14) from emitting large numbers of secondary X-ray photons, thus creating high background levels.

BRIEF DESCRIPTION OF THE DRAWINGS

Other objects and advantages of the invention will become apparent upon reading the following detailed description and upon reference to the accompanying drawings in which:

FIG. 3 is a diagram of an apparatus for detecting the presence of light elements on a surface of a semiconductor substrate using X-ray fluorescence (XRF);

Figure 1:
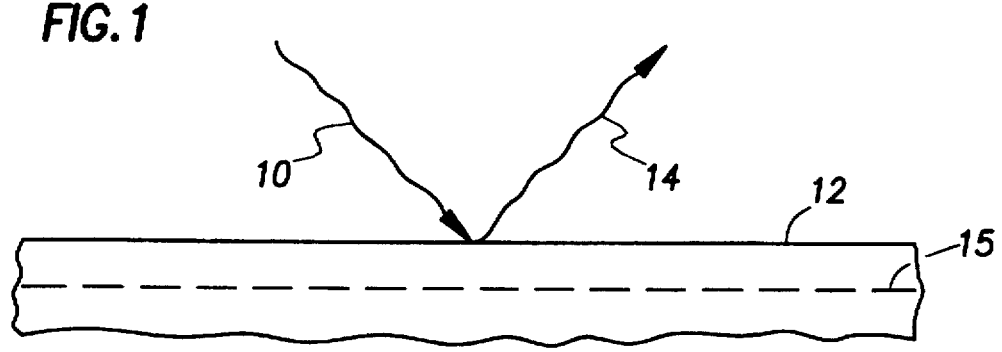
FIG. 1 shows a primary X-ray photon incident upon a target material, and a resulting secondary X-ray photon being emitted by the target material.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

The X-ray region of the electromagnetic spectrum gives rise to electromagnetic phenomena not measurable with optical techniques. The X-ray region of the electromagnetic spectrum includes frequencies from $1.0 \times 10^{17}$ Hz to $1.0 \times 10^{21}$ Hz. X radiation displays familiar wave characteristics such as refraction, polarization, diffraction, and scattering. Refractive indices of substances are nearly unity at X-ray frequencies, which means neither mirrors nor lenses can be fashioned for X-ray radiation. Reflection in the X-ray region occurs only at grazing angles of incidence (i.e., very small angles of incidence relative to the surface of the target).

X-ray fluorescence spectrometry is known in its application to elemental analysis. When electrically charged particles with sufficient energy strike a target material, X-ray photons are produced. Plotting the number of X-ray photons produced with a given wavelength in a given unit of time allows determination of a spectral pattern characteristic of the target material. Such a spectral pattern includes intensity peaks characteristic of the target material superimposed on a background X-ray radiation continuum.

Figure 2A:
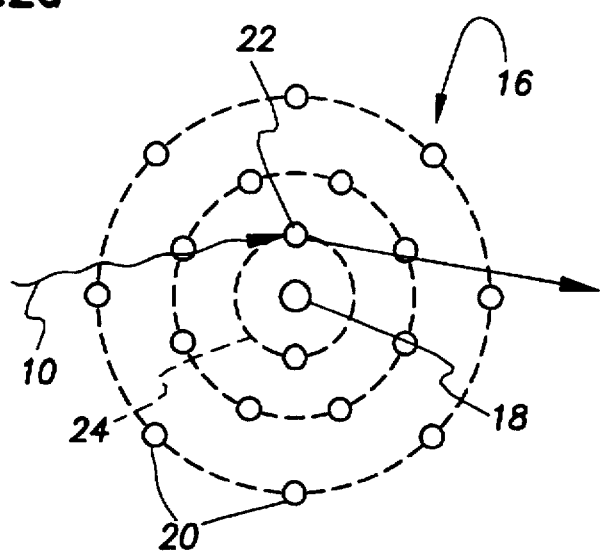
FIG. 2a shows the primary X-ray photon of FIG. 1 impacting an atom of the target material, and the resulting ejection of an electron from the innermost K electron shell of the atom.
Figure 2B:
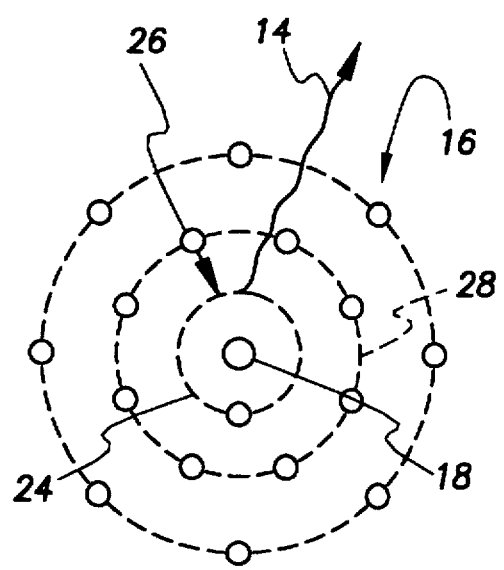
FIG. 2b shows an electron in the L electron shell of the atom of the target material of FIG. 2a filling the vacancy Created in the K electron shell, and the simultaneous emission of the secondary X-ray photon.

FIGS. 1, 2a, and 2b will be used to describe in general how X-ray fluorescence occurs within the realm of the present invention. FIG. 1 shows a primary X-ray photon 10 incident upon a target material 12, and a resulting secondary X-ray photon 14 being emitted from target material 12. X-ray photon absorption and emission occur at the atomic level. FIG. 2a shows an atom 16 of target material 12. In the simple atomic model shown, atom 16 has a nucleus 18 surrounded by electrons 20 at different discrete distances from nucleus 18 called electron shells. A given electron shell has a binding energy level equal to the amount of energy required to remove an electron from the electron shell. The binding energy level of an electron shell is inversely proportional to the distance of the electron shell from the nucleus. The innermost electron shell of an atom is called the K shell, and has the highest binding energy level associated with it. In FIG. 2a, K-shell electron 22 is located in K shell 24.

FIG. 2a also shows primary X-ray photon 10 impacting atom 16 within a target material 12. If the energy level of primary X-ray photon 10 (E) is greater than the binding energy level of a K shell 24 ($\phi_k$) the entire energy of primary X-ray photon 10 is absorbed by atom 16, and one of the electrons in K shell 24 is ejected from atom 16 of target material 12. As depicted in FIG. 2a, K-shell electron 22 is ejected from atom 16 after primary X-ray photon 10 is absorbed by atom 16 of target material 12. K-shell electron 22 is ejected with a kinetic energy of (E–$\phi_k$).

With a vacancy in K shell 24, atom 16 of target material 12 is energetic and unstable. The most probable stabilization mechanism is the filling of the vacancy in K shell 24 by an electron located in an electron shell with a lower binding energy level. As shown in FIG. 2b, an L-shell electron 26 in L shell 28, farther from nucleus 18 than K shell 24, may fill the vacancy in K shell 24. As L-shell electron 26 fills the vacancy in K shell 24, atom 16 may simultaneously emit secondary X-ray photon 14 with energy ($\phi_k-\phi_L$), where $\phi_L$ is the binding energy level of L shell 28. With a vacancy now in L shell 28, ionized atom 16 of target material 12 is more stable and less energetic.

X-ray fluorescence spectrometry permits examination of a target material from the surface of the target material down to a maximum escape depth of secondary X-ray photons. An escape depth 15 of secondary X-ray photon 14 is illustrated in FIG. 1.

FIG. 3 is an exemplary embodiment of an apparatus allowing detection of atoms of light elements with atomic numbers between 3 and 13. This apparatus includes a high-power X-ray source 30, a first collimator 32, a first multilayer crystal 34, a focusing capillary 36, a second collimator 38, and a second multilayer crystal 40. While three X-ray detectors 42a–c are also shown, it is noted that the number of X-ray detectors employed may range from one to eleven. A planar backside surface of a semiconductor substrate 44 is placed upon a flat upper surface of a wafer chuck 46, allowing a planar frontside surface of semiconductor substrate 44 to be exposed during analysis.

High-power X-ray source 30 includes a tungsten filament 48, a cathode 50, a rotating anode 52, and a beryllium window 54 located in a wall of a chamber 56. Air is evacuated from chamber 56 prior to and during use in order to reduce absorption of long wavelength X-ray photons within chamber 56. During use, an electric current is passed through tungsten filament 48 so as to heat tungsten filament 48 to incandescence. In this state, tungsten filament 48 gives off electrons through thermionic emission. Disc-shaped rotating anode 52 is caused to rotate about an axis perpendicular to its major planar faces, and is held at ground potential during use. Cathode 50 is charged to a highly negative potential in reference to rotating anode 52. An electron beam 58 is formed as electrons are accelerated toward rotating anode 52 in the electric field generated between cathode 50 and rotating anode 52. As the highly accelerated electrons strike electrons within atoms of rotating anode 52 and lose kinetic energy, X-ray photons are emitted from rotating anode 52 and exit through beryllium window 54. The walls of chamber 56 are typically made of thick metal in order to prevent X-ray photon penetration. A suitable high-power X-ray source having some of the advantages herein described may be obtained from the Rigaku Co., Osaka, Japan.

Rotating anode 52 comprises one or more elements which produce X-ray photons with sufficient energy (i.e., sufficiently short wavelengths) to cause atoms of light elements to emit secondary X-ray photons. Suitable elements include rubidium, tungsten, platinum, rhodium, and chromium.

Due to intensity losses in the apparatus, high-power X-ray source 30 must produce a large number of X-ray photons per unit time. As a result, a large number of electrons must bombard rotating anode 52 per unit time. A great deal of heat energy is generated during this process. If this heat energy is not dissipated rapidly, the anode material will melt. Causing rotating anode 52 to rotate about an axis perpendicular to its major planar surfaces continuously changes the area of the surface being bombarded by electrons, allowing the resulting heat energy to be dissipated in the mass of the anode. This prevents zonal melting of the anode material in the relatively small area where electrons strike rotating anode 52.

Figure 4:
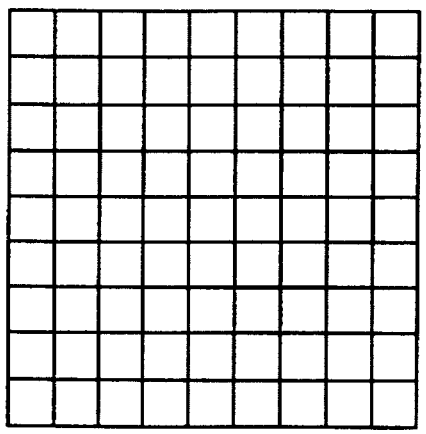
FIG. 4 is a cross-sectional view of a typical Soller-type collimator.

The X-ray photons produced by high-power X-ray source 30 follow divergent paths, and have many different wavelengths (energy levels). Thus high-power X-ray source 30 produces a divergent source of polychromatic X-ray radiation. First collimator 32 receives divergent polychromatic X-ray beam 60 produced by high-power X-ray source 30 and produces a quasi-parallel X-ray beam 62. First collimator 32 is preferably a Soller-type collimator having a bundle of straight, hollow metal conduits. FIG. 4 is a cross-sectional view of a typical Soller-type collimator. Fine collimation is obtained (at a cost of beam intensity) using spacings of about 1.0 micron between opposite walls of the individual square conduits making up the collimator. Suitable Soller-type collimators are commercially available from the Philips Co., Mahwah, N.J.

Figure 5:
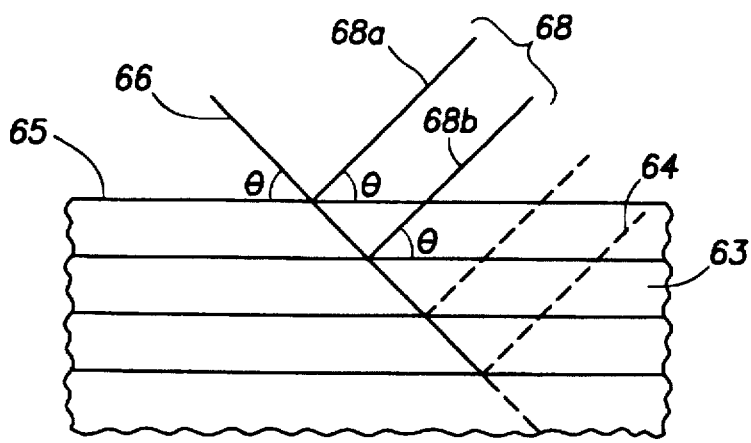
FIG. 5 is a partial cross-sectional view of a multilayer crystal showing incident and reflected X-ray beams.

A quasi-parallel X-ray beam is required for the proper operation of first multilayer crystal 34. A typical multilayer crystal consists of alternating layers of low and high atomic number elements (e.g., tungsten and carbon) formed upon a planar substrate. FIG. 5 is a partial cross-sectional view of an upper portion such a multilayer crystal. The multilayer crystal of FIG. 5 consists of alternating layers of a first layer 63 and a second layer 64. First layer 63 may be a layer of a low atomic number element, and second layer 64 may be a layer of a high atomic number element. Alternately, first layer 63 may be a layer of a high atomic number element, and second layer 64 may be a layer of a low atomic number element. In either case, first layer 63 and second layer 64 are made from elements with different refractive indices, and each layer is only a few atoms thick.

A small fraction of an incident X-ray beam 66 is reflected at a planar upper surface 65 of the multilayer crystal and at each interface between first layer 63 and second layer 64. The angle $\theta$ formed between incident X-ray beam 66 and upper surface 65 is equal to the angle formed between reflected X-ray beam 68a and upper surface 65, and to the angle formed between reflected X-ray beam 68b and the planar interface between first layer 63 and second layer 64. The intensity of reflected X-ray beam 68 is the sum of individual contributions from reflected X-ray beams 68a and 68b. For an arbitrary angle $\theta$ there is no special phase relationship between reflected X-ray beams 68a and 68b. In this case, reflected beams 68a and 68b interfere with one another, and the intensity of reflected X-ray beam 68 is very small. For certain angles of $\theta$, however, the extra distance traveled by reflected X-ray beam 68b is an integer number of the wavelengths longer than the distance traveled by reflected X-ray beam 68a. In this case, reflected X-ray beams 68a and 68b are in phase and reinforce one another, producing a strong reflected X-ray beam 68. This phenomenon is known as diffraction. Suitable common multilayer crystals for X-ray spectrometry operate as described at the desired wavelengths. Such multilayer crystals are commercially available from the Ovonix Co., Minneapolis, Minn.

The angle formed between incident X-ray beam 62 and first multilayer crystal 34 is chosen such that the wavelength of X-ray beam 70 produced by first multilayer crystal 34 corresponds to energy levels less than those necessary to cause silicon atoms (atomic number 14) in semiconductor substrate 44 to emit secondary X-ray photons. Since the critical excitation energy for silicon is about 1.8 keV, and the corresponding wavelength is about 6.7 angstroms, the angle formed between incident X-ray beam 62 and first multilayer crystal 34 is chosen such that the wavelength of X-ray beam 70 produced by first multilayer crystal 34 is greater than 6.7 angstroms. Thus the corresponding energy levels of X-ray photons in X-ray beam 70 are less than 1.8 keV. Contributions from X-ray photons with wavelengths differing from the desired wavelength will interfere with one another, largely canceling each other. Thus X-ray beam 70 produced by first multilayer crystal 34 is monochromatic (i.e., made up of photons with the same wavelength). The energies of X-ray photons of X-ray beam 70 are sufficient to excite secondary X-ray photon emissions from atoms of light elements (atomic numbers 3–13) but not atoms of heavier elements (atomic numbers 14 and greater). This prevents a relatively large number of secondary X-ray photons emitted by silicon atoms from creating a large background intensity level.

Figure 6:
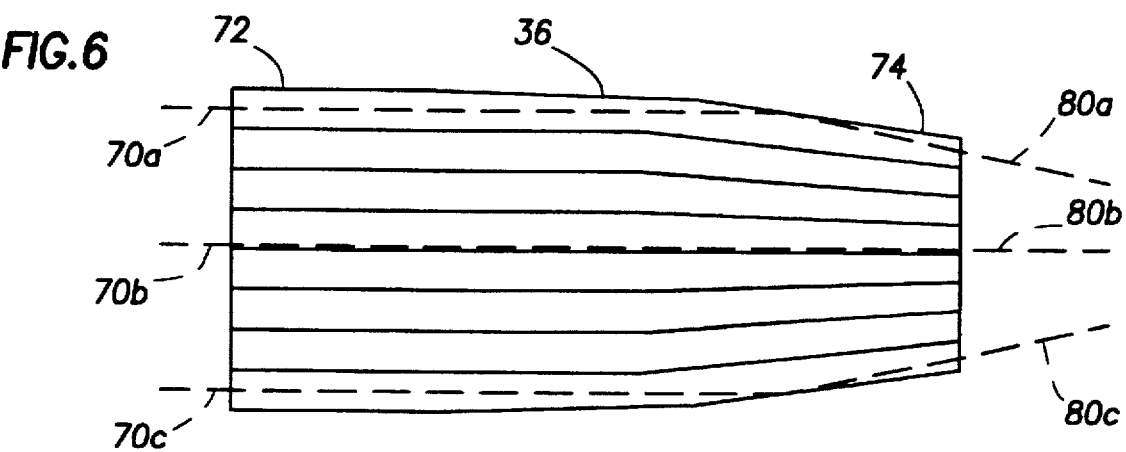
FIG. 6 is a cross-sectional view of a focusing capillary sliced parallel to paths of X-ray photons entering the focusing capillary.
Figure 7:
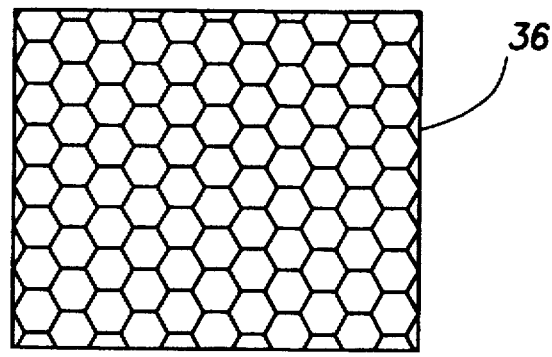
FIG. 7 is a cross-sectional view of a focusing capillary sliced perpendicularly to the paths of X-ray photons passing through the focusing capillary.

Focusing capillary 36 relies on high reflectivities at grazing angles of incidence to focus the X-ray photons of monochromatic X-ray beam 70 into a convergent X-ray beam 80 and onto a small circular area on the surface of semiconductor substrate 44. Focusing capillary 36 is a bundle of tiny conduits with internal dimensions which decrease from an entrance end to an exit end. FIG. 6 is a cross-sectional view of focusing capillary 36 sliced parallel to paths of X-ray photons as they enter an entrance end 72 of focusing capillary 36. X-ray photons travel through focusing capillary 36, and exit an exit end 74 of focusing capillary 36. Conduits in the middle of the bundle are straight, while the exit ends of conduits toward the outside of the bundle are bent toward the center of the bundle. As a result, X-ray photons following path 70b in the center of the bundle pass through the conduit without impacting an inner wall of the conduit. X-ray photons following paths 70a and 70c at the outer edge of the bundle cannot pass through the conduits without impacting an inner wall. The curvature of the inner walls of conduits at the outside of the bundle are such that X-ray photons following paths 70a and 70c impact an inner wall and are reflected toward a focal point some distance from exit end 74 of focusing capillary 36. FIG. 7 is a cross-sectional view of focusing capillary 36 sliced perpendicularly to paths of X-ray photons passing through focusing capillary 36. In the implementation illustrated, the conduits making up focusing capillary 36 have hexagonal cross sections. The distances between opposing inner walls of the conduits at entrance end 72 of focusing capillary 36 are about 1.0 micron. Suitable focusing capillaries are commercially available from the XOS Co., Albany, N.Y.

The circular area on the surface of semiconductor substrate 44 illuminated by convergent X-ray beam 80 has a diameter ranging from about 0.5 mm to about 10.0 mm. If the energies of photons in X-ray beam 80 are sufficient, any light elements present in the illuminated circular area will emit secondary X-ray photons at characteristic wavelengths (energy levels). Secondary X-ray photons will be emitted in all directions. Some of the secondary X-ray photons will follow paths within X-ray beam 82, and will enter second collimator 38.

Second collimator 38 has the same function as first collimator 32, producing a quasi-parallel polychromatic X-ray beam 84 from divergent polychromatic X-ray beam 82. Second collimator 38 is preferably a Soller-type collimator.

As with first multilayer crystal 34, a quasi-parallel X-ray beam is required for the proper operation of second multilayer crystal 40. FIG. 5 and the associated description of first multilayer crystal 34 also apply to second multilayer crystal 40. Second multilayer crystal 40 is mounted such that it is free to rotate about an axis 86 through the center of second multilayer crystal 40. Rotating second multilayer crystal 40 about axis 86 changes the angle formed between incident X-ray beam 84 and a planar upper surface of second multilayer crystal 40.

When multilayer crystal 40 is in a first position 88a, reflected photons of quasi-parallel X-ray beam 84 which reinforce one another produce a strongly-reflected monochromatic X-ray beam 90a. First position 88a is chosen such that the angle formed between incident X-ray beam 84 and the upper surface of second multilayer crystal 40 produces a strong reflection for X-ray photons with a wavelength (energy level) corresponding to a characteristic secondary X-ray emission of a first light element. X-ray beam 90a illuminates X-ray detector 42a. Thus X-ray detector 42a detects only secondary X-ray photons emitted by atoms of the first light element within a maximum escape depth of the surface of semiconductor substrate 44.

A second position 88b is chosen such that the angle formed between incident X-ray beam 84 and the upper surface of second multilayer crystal 40 produces a strong reflection for X-ray photons with a wavelength (energy level) corresponding to a characteristic secondary X-ray emission of a second light element. When multilayer crystal 40 is in second position 88b, reflected photons of quasi-parallel X-ray beam 84 which reinforce one another produce a strongly reflected monochromatic X-ray beam 90b. X-ray beam 90b illuminates X-ray detector 42b. Thus X-ray detector 42b detects only secondary X-ray photons emitted by atoms of the second light element within escape depth of the surface of semiconductor substrate 44. Up to 11 detectors may be installed and associated positions of second multilayer crystal 40 determined to correspond to secondary X-ray emissions of each of the 11 light elements.

X-ray detectors 42a–c are configured to detect incident X-ray photons and produce an electrical output signal. Suitable components for X-ray detectors 42a–c include common proportional detectors and scintillation X-ray detectors. Sealed or flow types of proportional detectors may be used to detect long wavelength X-ray photons emitted by light elements. One popular type of scintillation X-ray detector includes a thallium-doped sodium iodide crystal and is capable of detecting short wavelength X-ray photons. Such a detector is known as a NaI(Tl) scintillation detector. Suitable proportional counters and scintillation detectors are commercially available from the Harshaw Co., Solon, Ohio.

Figure 8:
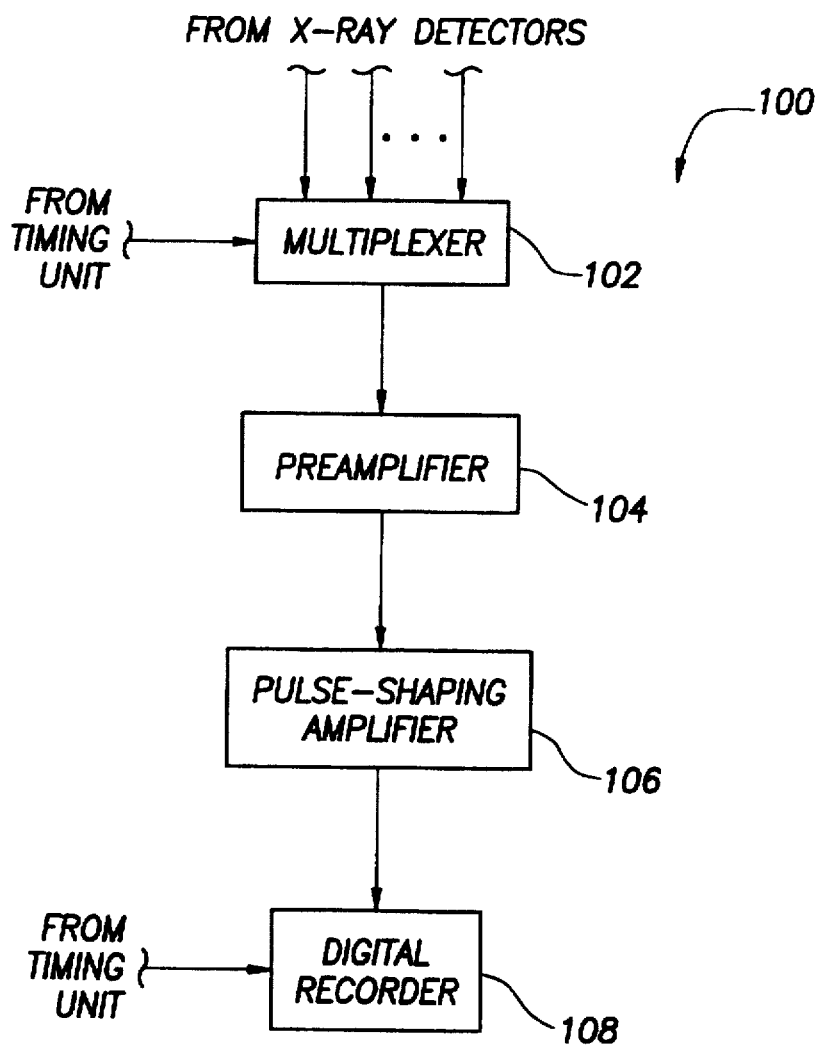
FIG. 8 is a block diagram of a suitable measurement system according to the present invention.

Electrical cables with connectors 92a–c connect X-ray detectors 42a–c to a measurement system (not shown). FIG. 8 is a block diagram of a suitable measurement system. A multiplexer 102 has input signals from X-ray detectors and a control input signal from a timing unit (not shown). The timing unit also controls the length of time second multilayer crystal 40 remains in a given position. Multiplexer 102 provides as an output signal the input signal from the X-ray detector currently illuminated by proper positioning of second multilayer crystal 40.

A typical X-ray detector functions as a photon-to-charge transducer, converting the energy of a detected X-ray photon into an electrical charge pulse. The amount of charge produced by an X-ray detector is proportional to the energy level of the detected X-ray photon. A preamplifier 104 converts input charge pulses from multiplexer 102 into high amplitude voltage pulses. A pulse-shaping amplifier 106 provides additional amplification and eliminates much of the "tail" of the voltage pulse occurring after the pulse peak.

A digital recorder 108 has an input signal from pulse-shaping amplifier 106 and a control input signal from the timing unit. Digital recorder 108 stores the number of X-ray photons detected by X-ray detectors in memory locations of a memory subsystem. Each detected X-ray photon thus represents a "count." Memory locations where counts are stored are selected based on the control signal from the timing unit such that the count associated with each X-ray detector is stored in a different memory location. After testing, the count associated with each X-ray detector (i.e., each light element) may be retrieved and analyzed.

During use, second multilayer crystal 40 is maintained in each designated position for a predetermined amount of time. The measurement system counts the number of X-ray photons detected by each X-ray detector. The number of X-ray photons detected by an X-ray detector (i.e., the number of counts stored in a memory location of digital recorder 108 associated with a given X-ray detector) is directly proportional to the number of atoms of the corresponding light element within escape depth of the surface of semiconductor substrate 44.

Absorption of a primary X-ray photon by an atom of a light element on the surface of the semiconductor substrate results in the emission of a single secondary X-ray photon. Thus for a given number of primary X-ray photons (with sufficient energy) incident upon the surface of the semiconductor substrate per unit time, the number of secondary X-ray photons detected by an X-ray detector in a predetermined amount of time is directly proportional to the number of atoms of a corresponding light element on the surface of the semiconductor substrate.

Figure 9:
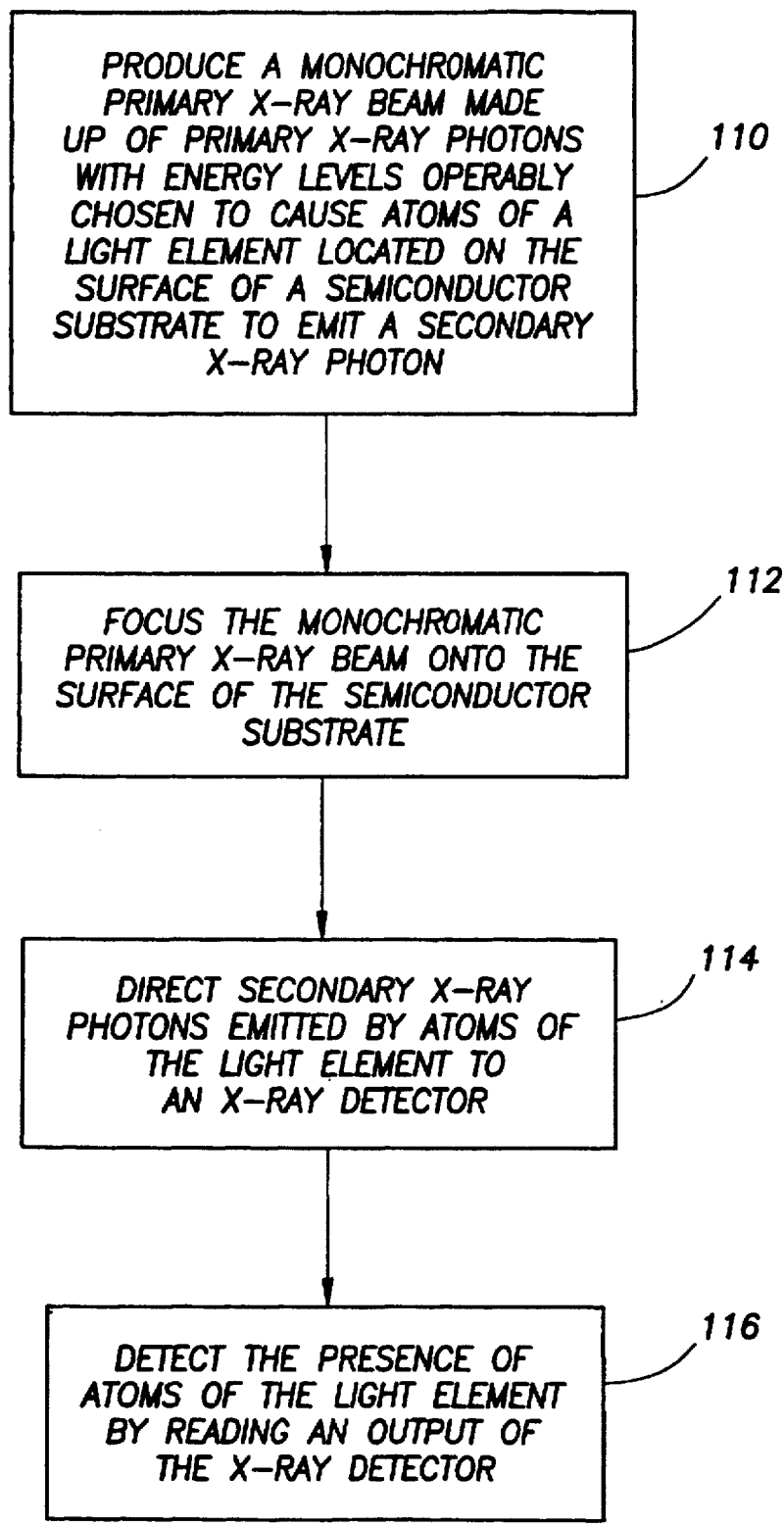
FIG. 9 is a flow chart describing a method of detecting the presence of one or more atoms of a light element located on a surface of a semiconductor substrate.

FIG. 9 is a flow chart describing a method of detecting the presence of one or more atoms of a light element located on a surface of a semiconductor substrate. During a first step 110, a monochromatic primary X-ray beam is produced which is made up of many primary X-ray photons. The energy level of each of the primary X-ray photons must be operably chosen to cause atoms of the light element to emit a secondary X-ray photon. In the above described apparatus, first collimator 32 and first multilayer crystal 34 work together to produce such a monochromatic primary X-ray beam from divergent polychromatic primary X-ray photons produced by high-power X-ray source 30. The monochromatic primary X-ray beam is then focused onto the surface of the semiconductor substrate during a step 112. Focusing capillary 36 in the above described apparatus focuses the monochromatic primary X-ray beam onto an exposed region of the surface of the semiconductor substrate. During a step 114, the resulting secondary X-ray photons emitted by atoms of the light element are directed to an X-ray detector. This function is carried out by second collimator 38 and second multilayer crystal 40 in the above described apparatus. The presence of atoms of the light element is detected by reading an output of the X-ray detector during a step 116. At least one detected secondary X-ray photon reveals the presence of at least one atom of the light element within the exposed region of the surface of the semiconductor substrate. In addition, the number of secondary X-ray photons detected by the X-ray detector is directly proportional to the number of atoms of the light element on the surface of the semiconductor substrate.

It will be appreciated to those skilled in the art having the benefit of this disclosure that this invention is believed to be capable of detecting the presence of light elements (i.e., elements with atomic numbers 3 through 13) on the surface of a semiconductor substrate. Furthermore, it is also to be understood that the form of the invention shown and described is to be taken as exemplary, presently preferred embodiments. Various modifications and changes may be made without departing from the spirit and scope of the invention as set forth in the claims. It is intended that the following claims be interpreted to embrace all such modifications and changes.

What is claimed is:

1. A method of detecting the presence of at atom located on a surface of a semiconductor substrate, comprising:

producing a monochromatic primary X-ray beam comprising a plurality of primary X-ray photons, wherein the energy level of each of the plurality of primary X-ray photons is operably chosen to cause the atom to emit a secondary X-ray photon;

focusing said monochromatic primary X-ray beam onto the surface of the semiconductor substrate;

directing a secondary X-ray photon emitted by the atom to an X-ray detector; and detecting the presence of the atom by reading an output of the X-ray detector.

2. The method as recited in claim 1, wherein the atom is associated with a light element having an atomic number between 3 and 13.

3. The method as recited in claim 1, wherein a plurality of atoms are located on the surface of the semiconductor substrate, and wherein a plurality of secondary X-ray photons are emitted by the plurality of atoms.

4. The method as recited in claim 3, wherein a portion of said plurality of secondary X-ray photons are detected by the X-ray detector, and the number of secondary X-ray photons detected by the X-ray detector is proportional to the number of said plurality of atoms.

5. The method as recited in claim 1, wherein the monochromatic primary X-ray beam is focused onto an exposed region of the surface of the semiconductor substrate using a focusing capillary, wherein said focusing capillary comprises a bundle of conduits with internal dimensions which decrease from an entrance end to an exit end.

6. The method as recited in claim 5, wherein the exposed region is circular and has a diameter ranging from about 0.5 mm to about 10.0 mm.

7. The method as recited in claim 1, wherein the directing step is accomplished using a collimator and a multilayer crystal arranged between the semiconductor substrate and the X-ray detector.

8. A method of detecting the presence of an atom located on a surface of a semiconductor substrate, comprising:

producing a monochromatic primary X-ray beam comprising a plurality of primary X-ray photons, wherein the energy level of each of the plurality of primary X-ray photons is operably chosen to cause the atom to emit a secondary X-ray photon;

focusing said monochromatic primary X-ray beam onto an exposed region of the surface of the semiconductor substrate using a focusing capillary, wherein said focusing capillary comprises a bundle of conduits with internal dimensions which decrease from an entrance end to an exit end;

directing a secondary X-ray photon emitted by the atom to an X-ray detector; and detecting the presence of the atom by reading an output of the X-ray detector.

9. The method as recited in claim 8, wherein the atom is associated with a light element having an atomic number between 3 and 13.

10. The method as recited in claim 8, wherein a plurality of atoms are located on the surface of the semiconductor substrate, and wherein a plurality of secondary X-ray photons are emitted by the plurality of atoms.

11. The method as recited in claim 10, wherein a portion of said plurality of secondary X-ray photons are detected by the X-ray detector, and the number of secondary X-ray photons detected by the X-ray detector is proportional to the number of said plurality of atoms.

12. The method as recited in claim 8, wherein the exposed region is circular and has a diameter ranging from about 0.5 mm to about 10.0 mm.

13. The method as recited in claim 8, wherein the directing step is accomplished using a collimator and a multilayer crystal arranged between the semiconductor substrate and the X-ray detector.

* * * * *